United States Patent [19]
Ismail et al.

[11] Patent Number: 5,561,944
[45] Date of Patent: Oct. 8, 1996

[54] METHOD AND APPARATUS FOR ENHANCING THE GROWTH AND QUALITY OF EDIBLE PLANTS

[75] Inventors: Sooliman Ismail; Brian Sacks, both of Johannesburg, South Africa

[73] Assignee: African Oxygen Limited, Johannesburg, South Africa

[21] Appl. No.: 135,219

[22] Filed: Oct. 12, 1993

[30] Foreign Application Priority Data

Nov. 4, 1992 [ZA] South Africa ............................ 92/8504

[51] Int. Cl.[6] .................................................... A01N 59/00
[52] U.S. Cl. .................................................... 47/58
[58] Field of Search ................................. 47/58.11, 58.12

[56] References Cited

U.S. PATENT DOCUMENTS 1,908,164  5/1933  Minor ........................................... 47/58

OTHER PUBLICATIONS

Dubey (1991) J. Environ. Biol. vol. 12, pp. 233–241.

Yao et al (1991) Water Research vol. 25, pp. 761–773.

Yao, et al. (1991) Water Research 25 (7):761–774 Dialog Abstract.

*Primary Examiner*—Che S. Chereskin
*Attorney, Agent, or Firm*—R. Hain Swope; David R. Draegert

[57] ABSTRACT

Method and apparatus for treating edible plants with feed water containing carbon dioxide and ozone while maintaining a growth maintaining effective amount of oxygen therein.

13 Claims, 1 Drawing Sheet

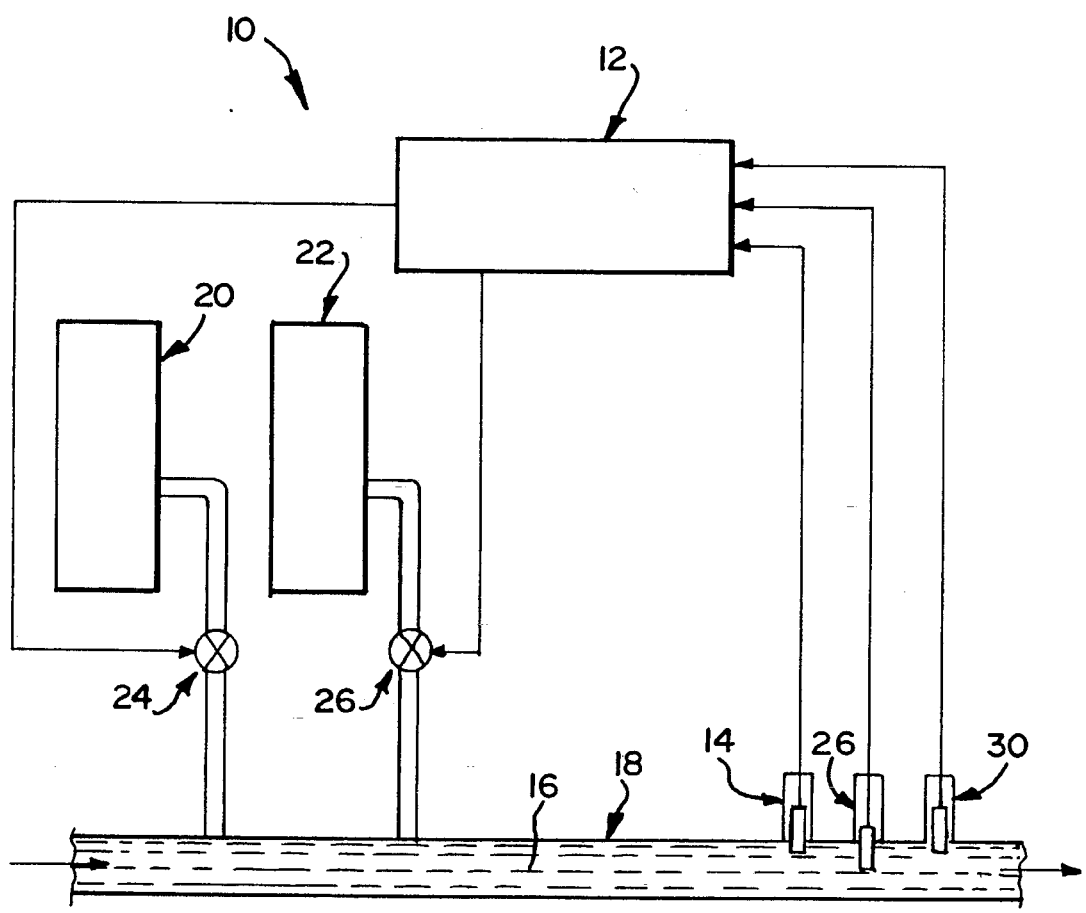

METHOD AND APPARATUS FOR ENHANCING THE GROWTH AND QUALITY OF EDIBLE PLANTS

TECHNICAL FIELD

The present invention is generally directed to a method and apparatus for enhancing the growth and quality of edible plants by treating the same with effective amounts of carbon dioxide and ozone.

BACKGROUND OF THE PRIOR ART

The yield and growth rate of edible plants such as agricultural produce including fruits, vegetables and grains are important to agricultural based industries. Improving the yield and growth rate of edible plants, as well as their appearance, taste and feel, enhances the value of edible plants both to the food industry and the consumer.

SUMMARY OF THE INVENTION

The present invention is generally directed to a method and apparatus for treating edible plants in a manner which improves growth, yield and the quality of the plant and foodstuffs obtained therefrom.

In particular, the present invention is directed to a method and apparatus of treating edible plants comprising treating the edible plants with feed water containing an effective amount of carbon dioxide and a biocidally effective amount of ozone, while maintaining a plant life-sustaining concentration of oxygen in the feed water.

In a preferred form of the invention, there is also provided means to detect the concentration of ozone and carbon dioxide, and/or oxygen in the feed water and to compare the same to a predetermined amounts of these gases that is desirable for enhancement of the edible plant. Means are provided for changing the amount of ozone and carbon dioxide in the feed water, if the amount detected in the feed water differs from the predetermined amount, until the detected amount is at least substantially the same as the predetermined amount of ozone and carbon dioxide.

BRIEF DESCRIPTION OF THE DRAWING

The following drawing is illustrative of an embodiment of the invention and is not intended to limit the invention as encompassed by the claims forming part of the application.

FIG. 1 is a schematic view of an embodiment of the edible plant treating system of the present invention.

DETAILED DESCRIPTION OF THE INVENTION

The method and apparatus of the present invention are particularly directed to treating edible plants such as agricultural produce, hereinafter exemplified by fruits and vegetables, with feed water containing effective amounts of ozone and carbon dioxide. The amount of ozone added to the feed water is a biocidally effective amount which means an amount of ozone which will be effective in reducing microbial activity in the edible plant, especially in the roots.

It will be appreciated that the concentration of ozone and carbon dioxide in the feed water will be maintained within a predetermined range of values depending upon various factors. Generally, most fruits and vegetables are satisfactorily treated according to the method of the present invention when the concentration of carbon dioxide in the feed water is maintained in the range of from 1 mg/l to 1,000 mg/l and the ozone in the range of from 1 mg/l to 500 mg/l. It is preferred that the relative proportion (mass per unit volume) of carbon dioxide and ozone be maintained in the range of 1:1 to 1:2.

Some free oxygen must be present in the feed water. It is typically not necessary in accordance with the present invention to add free oxygen since ozone converts to free oxygen in water after about 20 minutes. However, any free oxygen that might be required can be supplied by varying the concentration of ozone and the distance from the edible plants that the ozone is fed into the feed water so as to insure that ozone will have sufficient time to convert to free oxygen. In addition, or alternatively, the concentration of oxygen may be altered by varying the concentration of carbon dioxide in the feed water. Accordingly, it may be desirable to measure the concentration of oxygen in the feed water and to adjust the amount of ozone and/or carbon dioxide fed into the feed water.

The present invention preferably includes a system for controlling the concentration of ozone and carbon dioxide, and directly and/or indirectly oxygen, in the feed water. The system includes a device for measuring the concentration of the ozone and carbon dioxide in the feed water and regulating means connectable to respective supplies of ozone and carbon dioxide for regulating the delivery of the same to the feed water. The regulating means may operate by interrupting the supply of the ozone and carbon dioxide for an appropriate period of time to vary the concentration thereof in the feed water based on the amount of ozone and carbon dioxide detected in the feed water and the comparison thereof with a predetermined amount of ozone and carbon dioxide. Instead of, or in addition to, the regulating means may permit the rate at which the ozone and carbon dioxide is fed to the feed water to be varied. The regulation of the concentration of carbon dioxide and ozone in the feed water can serve to regulate the concentration of oxygen in the feed water.

The regulating means may be manually operated or may be automatically operated according to the particular value of the ozone and carbon dioxide concentration measurement at any time. Automatic operation may be provided, for example, via a data processor.

In one embodiment of the apparatus according to the invention, the measuring device may include an appropriate instrument or instruments positioned in the feed water for detecting the concentration of ozone and carbon dioxide and for transmitting a signal corresponding to the detected concentration. The signal is transmitted to a control means, such as a data processor, which determines whether or not a variation in the ozone and carbon dioxide concentration is required and adjusts the ozone and carbon dioxide regulating means accordingly. The regulating means may comprise a pneumatic or hydraulic actuating valve, controllable by the data processor or the like, and may be located in a feed line from the respective ozone and carbon dioxide supply lines.

As previously indicated, the present invention may also include means for measuring the concentration of oxygen in the feed water. Changes to the concentration of oxygen can be made by changing the amount of ozone and/or carbon dioxide added to the feed water as described above or by providing a separate source of oxygen to the feed water.

Depending on the properties of any other substance or composition that may be required to be added to the feed water, it may be desirable to supply the ozone and carbon dioxide and such other substance or composition as a mixture thereof in desired relative proportions. Instead, such other substance or composition may be fed to the feed water separately from the ozone and carbon dioxide, and the method then may include monitoring and optionally controlling the concentration of said other substance or composition in the feed water, and/or the relative proportions therein of the ozone and carbon dioxide and such other substance or composition.

Referring to FIG. 1, the system 10 includes a data processor 12, a measuring device 14 for measuring the amount of oxygen in the feed water 16 flowing through a supply line 18, a carbon dioxide supply 20 and an ozone supply 22 connected to the line 18 via pneumatic or hydraulic actuating valves 24 and 26. The ozone and carbon dioxide may be supplied from any conventional source. For example, the ozone may be supplied from an ozone producing system using an electric arc or ultraviolet light.

Devices 28 and 30 are provided to measure the amount of carbon dioxide and ozone, respectively, in the feed water 16. The data processor 12 is electrically or electronically linked to the measuring devices 14, 28 and 30 from which it can receive information pertaining to the amount of the respective gases in the feed water, and further is electrically or electronically linked to the actuating valves 24 and 26. Operation of the actuating valves 24 and 26 is preferably under the control of the data processor 12.

In use, ozone and carbon dioxide are fed into the feed water 16 from the ozone and carbon dioxide supplies 20 and 22 via the actuating valves 24 and 26, respectively. The carbon dioxide and ozone concentration downstream from the carbon dioxide and ozone supplies 20, 22 are continuously or intermittently monitored via the measuring devices 28, 30, respectively, and data processor 12.

When the oxygen concentration in the feed water 16 falls below a predetermined minimum value, one or both of the valves 24 and 26 receive(s) an appropriate signal from the data processor 12 and interrupts or reduces the feeding rate of the carbon dioxide supply and/or increases the rate of ozone supply to the feed water 16 to allow the oxygen concentration to rise. When the data processor 12, via the measuring device 14, detects an acceptable increase in the oxygen concentration in the feed water 16, a signal is sent to the valve 24 to reopen the supply of carbon dioxide and thereby allows carbon dioxide to enter into the feed water 16 once again and/or a signal is sent to the valve 26 to reduce the rate of ozone supply to the feed water 16.

When the respective concentrations or relative proportions of carbon dioxide and ozone fall outside the above-mentioned desired ranges, the valve(s) 24 and/or 26, as may be appropriate, receive(s) an appropriate signal from the data processor 12 and interrupts or reduces the feeding rate(s) of the carbon dioxide and/or ozone supply to the feed water 16 to allow the ozone or carbon dioxide concentration in the feed water to rise. When the data processor 12, via the measuring devices 28, 30, detects that the respective concentrations and relative proportions of carbon dioxide and ozone in the feed water 16 are acceptable, a signal is sent causing the valve(s) 24 and/or 26 to reopen in order to allow both carbon dioxide and ozone to enter into the feed water 16 to insure that an appropriate rate of carbon dioxide and/or ozone is provided to the feed water 16.

The method of the invention has been tested on edible produce such as fruit and vegetables. An increase in quality was detected insofar as texture, shape, color and taste of the fruit and vegetables is concerned. Furthermore, in appropriate cases, there was an increase in the fiber content of the fruit or vegetable and an increase in the carbohydrate and sugar content.

In a particular case, the method of the invention was used for tomato plants, as follows. Tomato seeds were planted in a conventional manner in two contiguous regions (i.e. region A and region B) of suitable agricultural land. The two regions A and B had been prepared for sowing in similar fashion to each other. In regards to fertilization, watering, pesticide and herbicide treatment, etc., the seeds, and thereafter the plants grown from such seeds, were treated in an identical manner except in one respect. That is, the method and device according to the present invention were used to feed carbon dioxide and ozone into the feed water and to control the concentration of oxygen in the plants of region A. Neither carbon dioxide nor ozone was added to the feed water of region B.

During the period commencing with initial watering of the seeds until about a month before harvesting of tomatoes from the plants grown from such seeds, carbon dioxide and ozone were fed into the feed water supply to region A in accordance with the method of the invention. The carbon dioxide concentration in this water supply was maintained at a value within the range 400 mg/l to 450 mg/l while the ozone concentration in this feed water supply was maintained at a value within the range 29 mg/l to 30 mg/l, and the oxygen concentration was not permitted to fall below 3 ppm. The sugar content of such tomatoes was found to be at least 1% more than tomatoes harvested from the plants grown in region B.

The procedure described above was repeated with tomato seedlings substituted for seeds. Similar results were obtained, the sugar content of tomatoes harvested from the plants grown from seedlings in region A being at least 1% more than the tomatoes harvested from the plants grown from seedlings in region B.

What we claim is:

1. A method of treating agricultural produce selected from the group consisting of fruits, vegetables, grains and combinations thereof comprising treating the agricultural produce with feed water containing an effective amount of carbon dioxide and a biocidally effective amount of ozone sufficient to reduce the microbial activity in the agricultural produce while providing a growth maintaining effective amount of oxygen in the feed water.

2. The method of claim 1 wherein the effective amount of carbon dioxide is from 1 mg/l to 1,000 mg/l of the feed water.

3. The method of claim 1 wherein the concentration of ozone is from 1 mg/l to 500 mg/l of the feed water.

4. The method of claim 1 wherein the growth maintaining effective amount of oxygen is at least 3 ppm of the feed water.

5. The method of claim 1 wherein the ratio of carbon dioxide to ozone is in the range of from 1:1 to 1:2.

6. The method of claim 1 further comprising measuring the amount of the ozone and carbon dioxide in the feed water and comparing the measured amount of ozone and carbon dioxide to a predetermined amount of ozone sufficient to reduce the microbial activity in the agricultural produce and a predetermined amount of carbon dioxide corresponding to said effective amount of carbon dioxide.

7. The method of claim 6 wherein the measured amount of at least one of ozone and carbon dioxide is different than the predetermined amount of ozone and carbon dioxide, said method further comprising regulating the amount of said at least one of ozone and carbon dioxide in the feed water until said amount is at least substantially the same as the predetermined amount.

8. The method of claim 7 wherein the step of regulating the amount of at least one of ozone and carbon dioxide in the feed water comprises intermittently supplying said at least one of said ozone and carbon dioxide to the feed water to thereby vary the concentration of oxygen in the feed water.

9. The method of claim 7 wherein the step of regulating the amount of at least one of ozone and carbon dioxide in the feed water comprises controlling the flow rate of said at least one of ozone and carbon dioxide into the feed water according to the difference between the measured amount of ozone and carbon dioxide and the predetermined amount.

10. The method of claim 6 further comprising adding another substance selected from the group consisting of fertilizers, pesticides, herbicides and combinations thereof to the feed water and regulating the rate of addition of said another substance to the feed water in order to maintain a predetermined concentration level.

11. The method of claim 1 wherein the edible plants are treated with the feed water at a pressure of about 10 bar.

12. The method of claim 7 further comprising measuring the amount of oxygen in the feed water, wherein if the oxygen concentration falls below a predetermined value, reducing the amount of carbon dioxide entering the feed water or increasing the amount of ozone entering the feed water or both.

13. The method of claim 7 further comprising measuring the amount of oxygen in the feed water, wherein if the oxygen concentration rises above a predetermined value, increasing the amount of carbon dioxide entering the feed water or reducing the amount of ozone entering the feed water, or both.

* * * * *